United States Patent [19]
Nath

[11] Patent Number: 5,675,689
[45] Date of Patent: Oct. 7, 1997

[54] ILLUMINATING EQUIPMENT WITH A LIQUID-FILLED LIGHT GUIDE

[76] Inventor: Günther Nath, Otto Heilmann Strasse 3, D-82031 Grünwald, Germany

[21] Appl. No.: 613,296

[22] Filed: Mar. 11, 1996

[30] Foreign Application Priority Data

Mar. 10, 1995 [DE] Germany ..................... 195 08 752.6

[51] Int. Cl.$^6$ ..................................................... G02B 6/20
[52] U.S. Cl. .............................. 385/125; 385/142; 385/901
[58] Field of Search ................................. 385/123, 125, 385/141–143, 901; 362/32

[56] References Cited

U.S. PATENT DOCUMENTS 4,009,382  2/1977  Nath .................... 362/32
4,747,662  5/1988  Fitz ..................... 385/125
4,995,699  2/1991  Lo ................... 385/125 X

*Primary Examiner*—John D. Lee
*Attorney, Agent, or Firm*—Helfgott & Karas, P.C.

[57] ABSTRACT

Illuminating equipment with a light source and a liquid light guide, which is coupled optically to the light source and the liquid core of which contains a mixture of heavy and light water in a ratio by volume of 50:50 to 98:2, depending on the length of the light guide. The light guide transfers the visible range of the spectrum in a color-neutral manner. At the same time, the long-wave radiation, which causes unwanted heating effects, is suppressed.

14 Claims, 1 Drawing Sheet

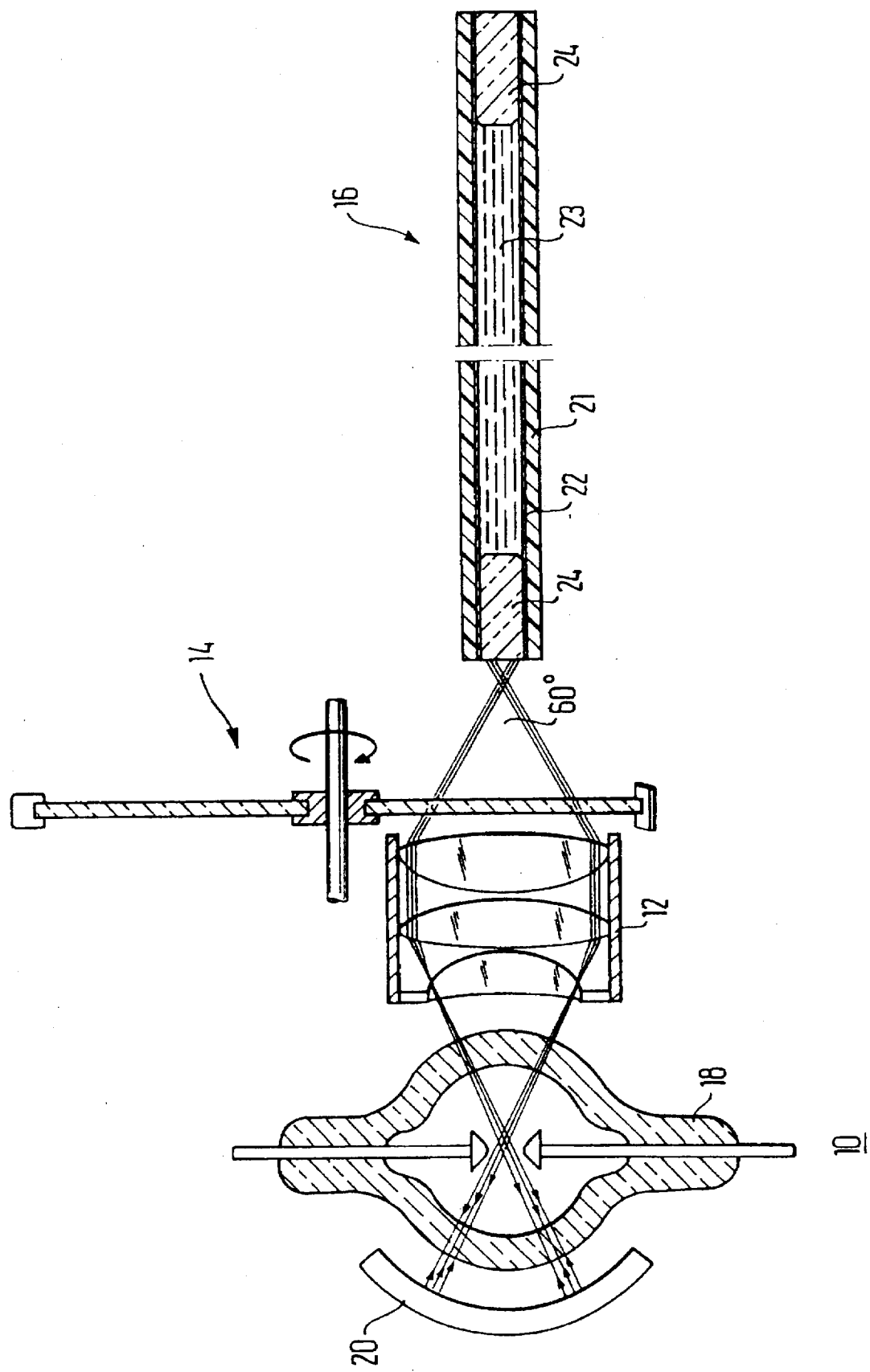

ILLUMINATING EQUIPMENT WITH A
LIQUID-FILLED LIGHT GUIDE

BACKGROUND OF THE INVENTION

The invention relates to illuminating equipment, particularly to illuminating equipment with a light source and a liquid-filled light guide.

The German utility pattern 94 00 445 discloses illuminating equipment with a light source and a liquid-filled light guide ("liquid light guide"), which is coupled optically with this light source and contains a cylindrical, tube-like envelope of a fluorine-containing polymeric material and a core of a light-conducting, aqueous liquid surrounded by the envelope. The envelope is coated on the inside with a thin layer of an amorphous copolymer, which is based on a combination of tetrafluoroethylene and a fluorine-containing cyclic ether. The copolymers, of which the inner layer consists, can be obtained from Dupont under the trade name of TEFLON AF®.

The U.S. Pat. No. 4,009,382 discloses a liquid light guide with a tube-like envelope of a fluorine-containing polymeric material and a liquid core, which can consist of a solution of an inorganic salt, such as calcium chloride, in very pure, heavy water.

The EP-C 246 552 discloses a liquid light guide, which contains a tube-like envelope of a fluorine-containing polymeric material consisting of copolymerized units of vinylidene fluoride and at least one further fluorine-containing monomer. Among the many other materials, solutions of salts in heavy water are also mentioned as material for the liquid core.

In the red region of the spectrum, the light absorption of heavy water ($D_2O$) is less than that of light water ($H_2O$), the spectral transmissivity of which decreases greatly from about 580 nm onwards. However, the region of higher spectral transmissivity of heavy water extends into the near infrared, so that, when heavy water is used as liquid for light guides, long-wave radiation is also transmitted. This long-wave radiation is hardly or not at all perceived by the human eye and generates heat in an illuminated object, which frequently is highly undesirable. This long-wave portion of the radiation, supplied by the light source, must then be eliminated by optical filters, which also absorb radiation in the useful, visible range, and are expensive and space consuming.

The known liquid light guides therefore enable transmissivity characteristics, corresponding to the sensitivity of the human eye, to be achieved only with additional expenditures. However, this is frequently required in practice, for example, when a color-neutral illumination and/or viewing of an object with an endoscope is required.

It is therefore an object of the present invention to provide illuminating equipment with a liquid light guide, which ensures a color-neutral light transfer and the liquid light guide of which has spectral transmissivity characteristics, which are adapted particularly well to the long wavelength end of the sensitivity of the human eye.

SUMMARY OF THE INVENTION

This objective is accomplished by illuminating equipment with a light source and liquid-filled light guide containing a tubular envelope of a fluorine-containing polymer and a core of an aqueous liquid. Further developments, as well as advantageous refinements of such illuminating equipment are the object of dependent claims.

Surprisingly, it has turned out that, with a light guide liquid, which contains a mixture of heavy water and about 2 to 50 percent by volume of light water as liquid phase, liquid light guides can be realized, the spectral transmissivity characteristics of which, particularly at the long wavelength end, are adapted very well to the sensitivity of the human eye, so that the illuminating equipment is capable of supplying neutral "white" light, which contains only a negligibly small proportion of undesirable long wavelength radiation, which generates heat. It is particularly advantageous that the ratio, in which the heavy water and the light water are mixed, can be selected as a function of the length of the light guide, so that the spectral transmissivity characteristics are relatively unvarying in the core, spectral range from about 400 to 720 nm, which is detected by eye (and by a light meter) and then show a steep decline towards longer wavelengths. The position of this steep decline can be influenced in an advantageous manner by the proportion of light water.

A preferred embodiment of the present illuminating equipment contains
a) a light source with a tungsten-halogen incandescent lamp or a gas-discharge or vapor-discharge lamp and
b) a light guide with
  b1) an envelope of TFP, FEP, PTFE, PFA, ETFE OR PCTFE (refer to the utility patent mentioned above), which is provided on the inside with
  b2) a layer of an amorphous fluorinated polymer based on a combination of tetrafluoroethylene and a cyclic ether (TEFLON AF) and with
  b3) a liquid core of a solution of calcium chloride in a mixture of heavy water with 5 or 10% by volume up to about 20 or 30% by volume of light water.
  b4) hydrochloric acid, preferably DCl, in an amount so that the pH value of the solution is between 4 and 6.5, preferable around 5.

BRIEF DESCRIPTION OF THE DRAWING

An example of the illumination equipment of the present invention is shown in the drawing.

DESCRIPTION OF THE INVENTION

The illuminating equipment, shown in a very simplified fashion in the drawing, contains a light source 10, a condenser 12 with three quartz lenses, optionally a filter revolver 14 and a light guide 16. In the case of the example shown, the light source contains a 200 W high-pressure mercury vapor lamp 18, type HBO 200, with a concave, spherical reflector. The light source may also contain a different gas-discharge or vapor discharge lamp and a tungsten-halogen projection lamp with a cold light reflector is preferred for many purposes.

The liquid light guide contains a flexible, tube-like envelope 21 of a fluoropolymer of the above-mentioned type. The envelope preferably consists of a material with a low refractive index (n=approx. 1.35), such as the terpolymer, Hostaflon TFB® of Hoechst, or the Teflons FEP, PTFE, PFA or TEFZEL ETFE® of Dupont or PCTFE (polychlorotrifluoroethylene) or PVDF (3M). On its inner surface, the envelope has a layer 22 of TEFLON AF, which is thin in comparison to the thickness of the wall, and is closed off by a cylindrical quartz window 24 at both of its ends. The thickness of the layer usually is a few micrometers.

As liquid phase, the liquid core 23 contains heavy water with at least 2 or 3% by volume and not more than 50% by volume of light water. In general, the concentration of light water varies inversely with the length of the light guide.

For a light guide, which transfers the visible range of the spectrum very well and, at the same time, suppresses the undesirable infrared optimally, the following proportions of light water in the mixture of heavy and light water, depending on the length of the liquid core, have turned out to be successful:

| Length of the Core | Percentage Light Water |
| --- | --- |
| Up to 1,000 mm | 50 to 30% by volume |
| 1,000 to 2,000 mm | 30 to 20% by volume |
| 2,000 to 4,000 mm | 20 to 10% by volume |
| 4,000 to 10,000 mm | 10 to 5% by volume |
| above 10,000 mm | 5 to 2% by volume |

EXAMPLE 1

Envelope 21: PEP, wall thickness 0.5 mm, length 2,000 mm, coated on the inside with TEFLON AF 1600, thickness of the internal coating approx. 4 μm
Core 23: calcium chloride, dissolved in 80% by volume of $D_2O$+20% by volume of $H_2O$.

The calcium chloride content is such that saturation in the temperature range normally employed (for example, from $-20°$ C. to $+40°$ C.) is essentially reached, but not exceeded.

The transmission of the light guide is high in the range from about 400 to 720 nm and then drops off very steeply towards longer wavelengths.

EXAMPLE 2

Envelope: length 3,000 mm, otherwise as for Example 1.
Core: as for Example 1, however with 10% by volume of $H_2O$.

EXAMPLE 3

Envelope and core as for Example 1; however, the length is 6,000 mm and the $H_2O$ content is 5% by volume.

EXAMPLE 4

Envelope and core as for Example 1; however, the length is 10,000 mm and the $H_2O$ content is 3% by volume.

EXAMPLE 5

Envelope 21: PEP, wall thickness 0.5 mm, length 1,000 mm, coated on the inside with TEFLON AF 2400, thickness of the internal coating approx. 2 μm
Core 23: $D_2O$ of high purity with 15% by volume of $H_2O$.

If the optional filter revolver 14 is provided, it has an empty position without a filter and one or more positions with optical filters, which alternatively permit the desired spectra/ranges for a color-selective illumination to be selected. For illuminating HPD or hematoporphyrin, the use of the present illuminating equipment with a filter, which transmits in the red range (600 to 700 nm) and a xenon or tungsten lamp as light source is advantageous.

The above examples can be modified by replacing calcium chloride with a different chloride, such as sodium chloride or zinc chloride, with a fluoride, such as potassium fluoride or cesium fluoride, or with a phosphate. Of course, the invention is not limited to the numerical values and materials given by way of example.

The light-conducting solution, also that of the above examples, has advantageously a pH value in the acid region, more specifically equal to or less than seven, preferably between 4 and 6.5. This reduces the tendency of the dissolved salt to crystallize out of the solution when the light guide is subjected to low temperatures, e.g., during shipment by air freight. Preferred are pH values around 5. The acidity of the solution may be adjusted to the desired pH value by adding hydrochloric acid, preferably DCl. Calcium chloride solution should be prepared by using $CaCl_2$ free of crystal light water.

What is claimed is:

1. Illuminating equipment with a light source and a liquid-filled light guide, which contains a tube-like envelope of a fluorine-containing polymer material having a given refractive index and a core of an aqueous liquid, said liquid having a refractive index larger than that of said polymer material so that light propagating within said liquid core is totally reflected at the core-envelope interface, said liquid core containing a mixture of heavy water and 2 to 50% by volume of light water.

2. The illuminating equipment of claim 1, characterized in that the inner surface of the envelope is coated with a layer of an amorphous polymer based on a combination of tetrafluoroethylene with a cyclic ether (Teflon AF).

3. The illuminating equipment of claim 1, characterized in that the mixture contains at least 5% by volume of light water.

4. The illuminating equipment of claim 1, characterized in that the mixture contains at least 10% volume of light water.

5. The illuminating equipment of claim 1, characterized in that the mixture contains at least 20% by volume of light water.

6. The illuminating equipment of claim 1, characterized in that the light source contains a tungsten-halogen incandescent lamp or a discharge lamp.

7. The illuminating equipment of claim 1, characterized in that the envelope consists of FEP.

8. The illuminating equipment as claimed in claim 1, wherein said core consists of a salt solution.

9. The illuminating equipment as claimed in claim 1, wherein said aqueous liquid is a salt solution having a pH value of at the most 7.

10. A liquid-filled light guide, which comprises a tube-like envelope of a fluorine-containing polymer material and a core of an aqueous liquid, wherein said liquid core is comprised of solution of calcium chloride in a mixture of heavy water and 2 to 20% by volume of light water and hydrochloric add in such an amount that the pH value of the solution is between 4 and 6.5.

11. The light guide as claimed in claim 10, wherein said hydrochloric add consists essentially of DCl.

12. The light guide as claimed in claim 10, wherein said light guide is coupled to a light source selected from the group of light sources consisting of tungsten-halogen incandescent lamps and discharge lamps.

13. A liquid-filled light guide, which comprises a tube-like envelope of a fluorine-containing polymer material and a core of an aqueous liquid, wherein said liquid core is comprised of a solution of calcium chloride in a mixture of heavy water and 2 to 20% by volume of light water and hydrochloric acid in such an amount that the pH value of the solution is at most 7.

14. The light guide as claimed in claim 13, wherein said light guide is coupled to a light source selected from the group of light sources consisting of tungsten-halogen incandescent lamps and discharge lamps.

* * * * *